United States Patent [19]

Schoenberg

[11] Patent Number: 4,888,001
[45] Date of Patent: Dec. 19, 1989

[54] COVER FOR A DISPOSABLE HYPODERMIC NEEDLE

[76] Inventor: Stephen J. Schoenberg, 124 Amherst Ave., Atherton, Calif. 94025

[21] Appl. No.: 200,935

[22] Filed: Jun. 1, 1988

[51] Int. Cl.⁴ .............................................. A61M 5/32
[52] U.S. Cl. ................................... 604/162; 604/192; 604/263
[58] Field of Search ............... 604/192, 263, 187, 171, 604/162, 272, 273

[56] References Cited

U.S. PATENT DOCUMENTS

| | | |
|---|---|---|
| 2,847,995 | 8/1958 | Adams . |
| 2,854,976 | 10/1958 | Heyrich ........................ 604/263 X |
| 3,323,523 | 6/1967 | Scislowicz et al. . |
| 3,574,306 | 4/1971 | Alden . |
| 3,658,061 | 4/1972 | Hall ..................................... 604/263 |
| 3,885,560 | 5/1975 | Baldwin . |
| 4,170,993 | 10/1979 | Alvarez . |
| 4,392,856 | 7/1983 | Lichtenstein . |
| 4,627,843 | 12/1986 | Raines . |
| 4,664,259 | 5/1987 | Landis . |
| 4,676,783 | 6/1987 | Jagger et al. . |
| 4,820,277 | 4/1989 | Norelli . |

Primary Examiner—John D. Yasko
Attorney, Agent, or Firm—Irell & Manella

[57] ABSTRACT

A disposable hypodermic needle is disclosed, including a conventional hollow needle having a sharp distal end and a plastic, integrally formed closure means, including a shank mounted on the distal end, plastic wings for enclosing the distal end for disposal of the needle. The wings include interlocking means to make the closure permanent, and include hinges for allowing the wings to be manipulated relative to the shank. Grips are provided on the wings for safe handling of the hypodermic needle. A sheath is provided for the distal end of the needle for maintaining its sterility and preventing accidental injury to the practitioner. In one embodiment, a lock hub is provided at one end of the shank to allow connection to a catheter, and in another embodiment, a tube is provided between the shank and the lock hub.

14 Claims, 5 Drawing Sheets

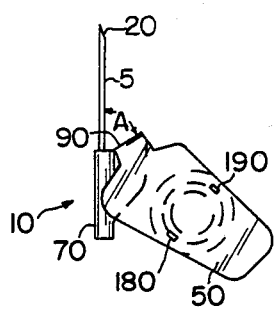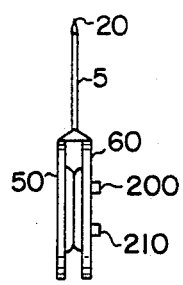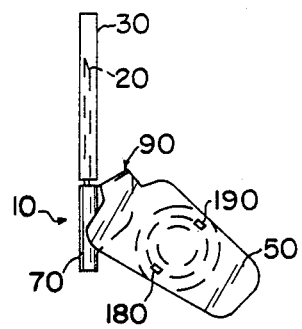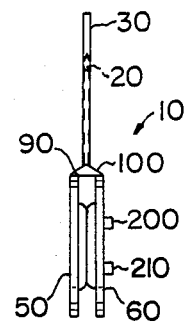
FIG.3B  FIG.3A  FIG.2B  FIG.2A
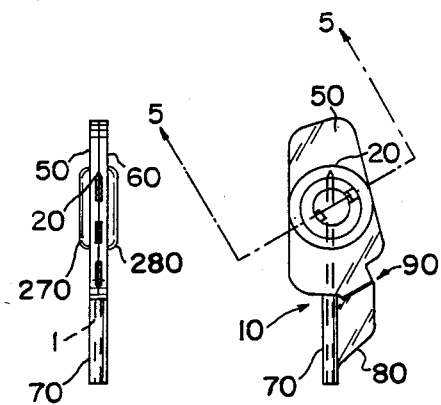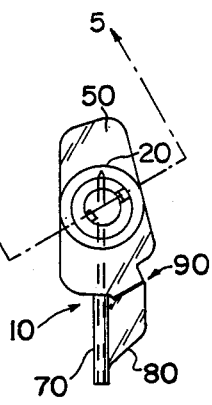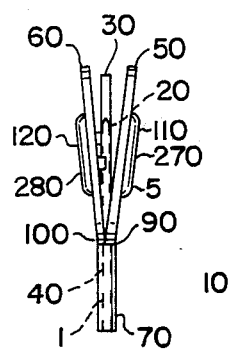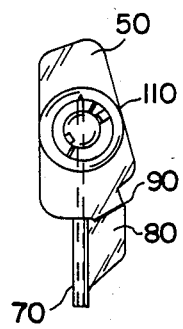
FIG.4A  FIG.4B  FIG.1A  FIG.1B

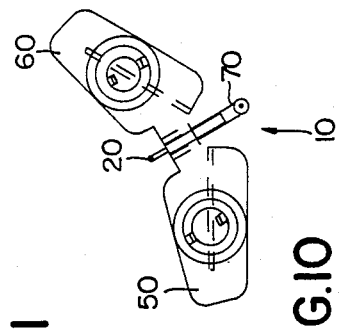
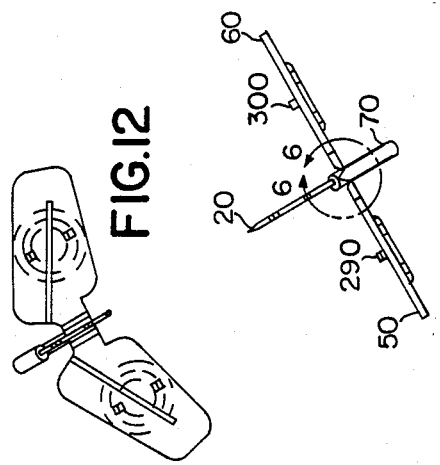
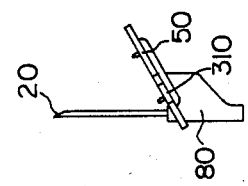
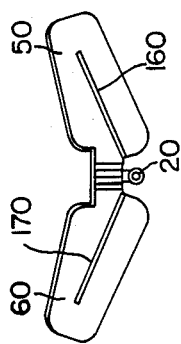
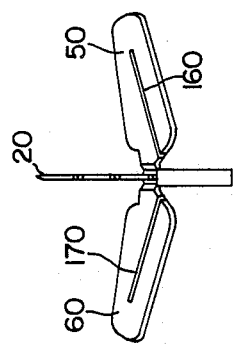

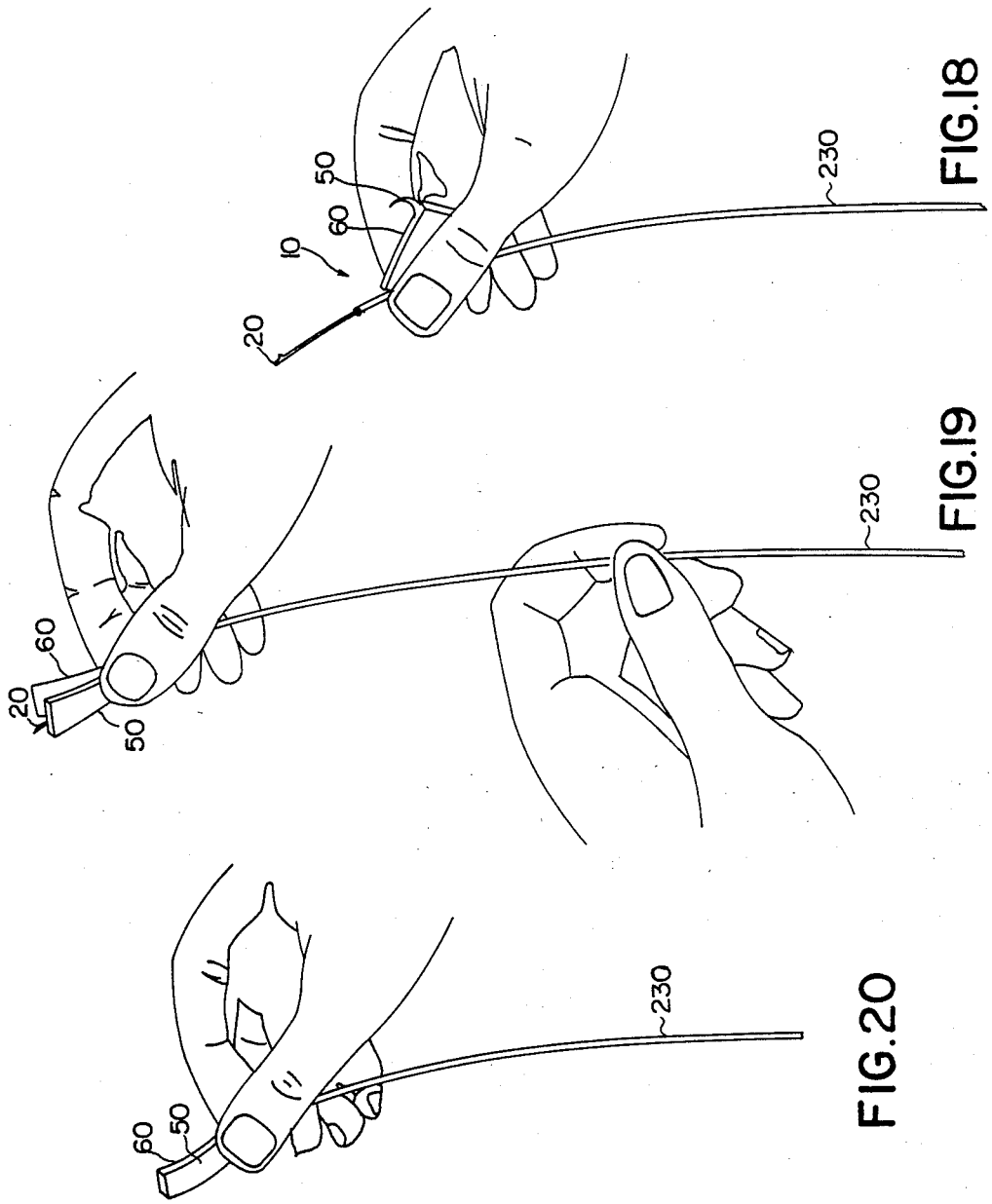

COVER FOR A DISPOSABLE HYPODERMIC NEEDLE

BACKGROUND OF THE INVENTION

This invention relates to hypodermic needles, and in particular to disposable needles which are for single uses only.

It is a chronic problem among doctors and nurses who utilize needles either for injecting patients or for connecting such needles to intravenous catheters that one is frequently punctured by a needle in the process of using it. Accidental injury from such needles occurs at several stages, including when the needle is first removed from its packaging for use, when the needle is actually being inserted into the patient or catheter, and when the needle is packaged for disposal.

Prior art devices have been developed in an attempt to solve these problems, by providing certain types of needle guards. Certain problems are inherent in the earlier devices, including the fact that the needle guards which are provided become inconvenient obstructions when one attempts to place the needle in the vein of the patient. Other needle coverings are difficult to replace over the needle after use, further engendering the risk of puncture to the nurse or doctor.

It is an object of this invention to provide a disposable hypodermic needle with minimal risk of puncture to the medical practitioner at any stage of use.

It is another object of this invention to provide such a needle which includes a protective cover which is safe for both handling and disposal.

It is a further object of the invention to provide a needle with such a cover which is convenient for use when the needle is left for an extended length of time in the vein of the patient.

Other objects, advantageous and features will more fully appear in the course of the following discussion.

SUMMARY OF THE INVENTION

A disposable hypodermic needle is provided, including a cannula with a proximal end and a sharp distal end, and a closure for the sharp distal end, the closure being made of plastic and integrally formed with a shank surrounding a portion of the proximal end. Obliquely angled or otherwise nonaxially aligned plastic hinges are provided on opposite sides of the shank, and the closure comprises two wings attached via these hinges to the shank. Additionally, a removable plastic sheath is provided to enclose the distal end of the needle and ensure sterility prior to use.

Each of the closure wings is provided with means for interlocking with the other closure wing, such as by means of locking tabs and closure ports, respectively. In addition, each closure wing is provided with a grip for sure handling by the medical practitioner.

In use, the medical practitioner first removes the sheath and then folds the wings back to a substantially coplanar contiguous configuration for inserting the needle into the patient. The wings may then be folded flat against the skin of the patient and affixed in place for an extended period. Upon removal, the wings are then folded together over the sharp distal end of the needle, and a groove is provided in each wing for receiving the distal end. The wings are interlocked together, and the needle may then be disposed of safely.

BRIEF DESCRIPTION OF THE DRAWINGS

FIG. 1A is an end view of a partially open disposable hypodermic needle having a cover incorporating the present invention;

FIG. 1B is a side view of the needle of FIG. 1A;

FIG. 2A shows a view similar to FIG. 1A, with the needle cover folded back;

FIG. 2B is a side view of the view of FIG. 2A;

FIG. 3A is a view like that of FIG. 2A, with the needle sheath removed;

FIG. 3B is a side view of FIG. 3A;

FIG. 4A is a view similar to FIG. 3A, with the needle cover closed over the end of the needle;

FIG. 4B is a side view of FIG. 4A;

FIG. 10 is a top view of the needle cover of the present invention in an open position;

FIG. 11 is a view of the needle and cover of FIG. 10 rotated by 90°;

FIG. 12 is a bottom view of the needle and cover of FIG. 11, rotated an additional 90°;

FIG. 13 is a view of the needle and cover of FIG. 11, rotated 90° in the plane of the closure wings shown in FIG. 11;

FIG. 14 is a view of the needle and cover of FIG. 13 rotated 90° about the axis of the needle;

FIG. 15 is a view of the needle and cover of FIG. 14, rotated 90° about a vertical plane containing the needle;

FIG. 18 is a view showing the manner of grasping the needle for removal from the arm of the patient;

FIG. 19 is a view showing the manner of closing the wings to cover the distal end of the needle; and FIG. 20 is a view of the needle and cover of the invention ready for disposal.

DETAILED DESCRIPTION OF THE PREFERRED EMBODIMENTS

Figure 5:
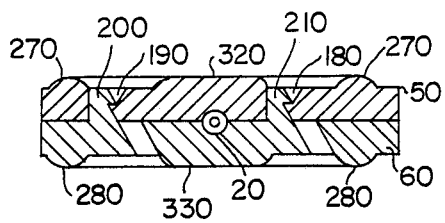
FIG. 5 is a sectional view taken along the line 5—5 of FIG. 4.

FIG. 1A shows a view of a disposable hypodermic needle having a cannula 5 with a cover 10 incorporating the present invention. The cannula 5 includes a proximal end 1 (shown in dotted fashion in FIGS. 1A and 4B) and a sharp distal end 20 which has a standard hollow configuration for insertion into a patient. Over the end 20 a removable, disposable sheath 30, preferably formed from plastic, is provided for protecting those handling the cannula 5 and for maintaining the sterility of the end 20.

The cannula 5 is conventionally formed from metal, and includes a portion 40 integral therewith. The needle cover 10 includes flaps or wings 50 and 60, a plastic shank 70 and a wing support portion 80, which are preferably formed of plastic and are integrally attached to one another. The plastic of which the wings, shank and support portion are formed should be a nontoxic, resilient plastic which can be easily sterilized such as in an autoclave. As will be seen below, it is an important feature that the plastic is resilient, and thus may be repeatedly bent or folded without deformation or rupture.

The wings 50 and 60, shank 70 and portion 80 are formed in the preferred embodiment from a single piece of plastic, such as by injection molding. Areas of reduced width form hinges 90 and 100 for allowing the wings 50 and 60 to be freely moved with respect thereto. Grips 110 and 120 are provided on the wings 50 and 60, respectively.

When the practitioner first removes the needle from its packaging, he folds the wings 50 and 60 back to the position shown in FIGS. 2A and 2B. He then removes the sheath 30, resulting the configuration shown in FIGS. 3A and 3B. At this point, the needle is ready for use.

Figure 7:
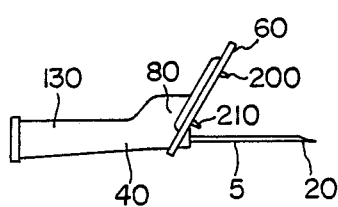
FIG. 7 is a side view of the needle cover of the present invention in an open position.
Figure 8:
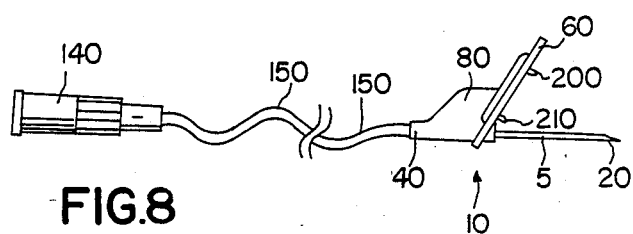
FIG. 8 is a view similar to that of FIG. 7 showing an alternative lock hub for catheter attachments.
Figure 9:
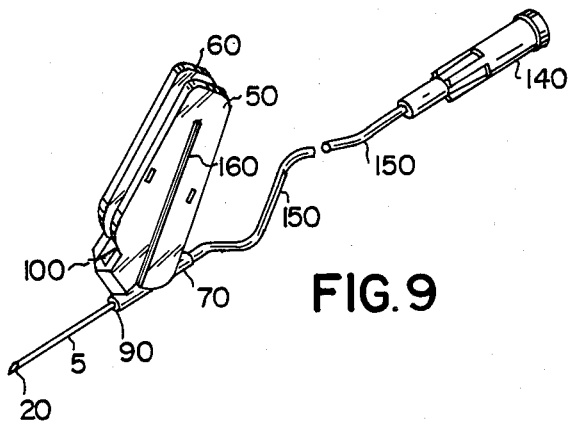
FIG. 9 is a perspective view of the needle cover of FIG. 8.

FIGS. 7 and 8 show two alternative embodiments of the invention, having lock hubs (known as "Luer lock hubs"). In FIG. 7, a lock hub 130 is provided which is integrally formed with the shank 40. In FIG. 8, a lock hub 140 is provided which is connected by means of a tube or catheter 150 to the needle cover 10. Either of the lock hubs 130 or 140 is connected to a catheter for providing drugs, nutrients or the like to the patient. It will be appreciated that, in FIGS. 7 and 8, the wings 160 lies in a plane perpendicular to the view shown. FIG. 9 shows a perspective view of the embodiment of FIG. 8, with the wings folded back upon one another.

For a complete understanding the structure of the invention, FIGS. 10–15 show various orthogonal views. Thus, FIG. 10 shows a top view of the needle cover 10 with the wings 50 and 60 in an open position. FIG. 11 is a view rotated 90° about a plane perpendicular to the wings in FIG. 10 and intersecting the axis of the distal end 20. FIG. 12 shows a view of the needle rotated another 90°.

FIG. 13 shows a view of the needle of FIG. 11 rotated in a plane containing the wings 50 and 60, and FIG. 14 shows a further 90° rotation about the axis containing the end 20. Finally, FIG. 15 shows a further 90° rotation in a plane containing the end 20, about an axis at right angles thereto.

As seen most clearly in FIGS. 9, 14 and 15, each wing 50 and 60 includes a groove such as grooves 160 and 170, respectively. In addition, wing 50 includes closure ports 180 and 190, and wing 60 including locking tabs 200 and 210. The uses for these grooves, ports and locking tabs are described below.

Figure 16:
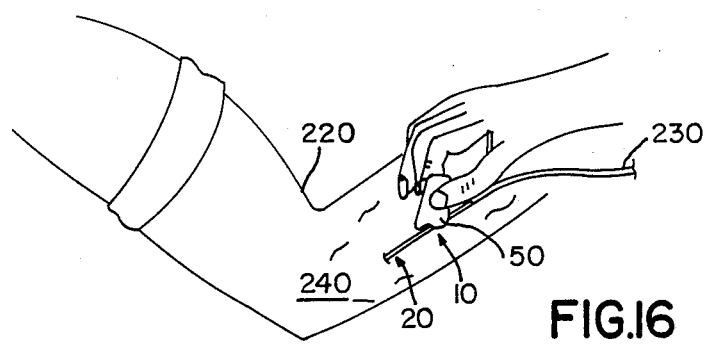
FIG. 16 is a perspective view of a needle and cover of the invention with the needle being inserted into the arm of a patient.

As mentioned, when the practitioner first removes the needle from its shipping package, he removes the sheath 30, thus exposing the distal end 20 of the cannula 5. The lock hub 130 or 140 is connected to a catheter 230 or to a syringe (not separately shown) in a conventional manner. The practitioner then grasps the needle cover 10 at the wings 50 and 60, as shown in FIG. 16, and proceeds to insert the distal end 20 into an arm 220 or other bodily part of a patient. As shown in FIGS. 3A, 3B and 16, when the wings 50 and 60 are folded back about their hinges 90 and 100, respectively, they lie substantially coplanar to one another and form a convenient grip for manipulating the needle. Indeed, once the needle cover 10 is first opened as shown in FIGS. 2A and 2B, it may thereafter be grasped by the grip formed by the wings 50 and 60, which considerably decreases the likelihood of the practitioner accidentally puncturing himself.

Once the needle is inserted into the arm 220, wing 50 is folded down about its hinge 90 such that it lies substantially flat against the skin 240 of the arm 220. The wing 50 is then taped into place by a piece of tape 250 shown in dotted fashion in FIG. 17.

Figure 17:
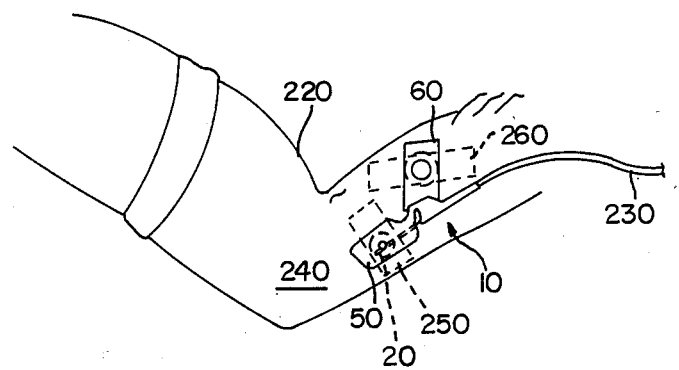
FIG. 17 is view similar to FIG. 16, showing affixiation of the needle in the arm of the patient for extended use.

Similarly, wing 60, due to the configuration of the hinge 100, can be folded flat against the skin 240, and is also taped in place by a piece of tape 260 shown in dotted fashion in FIG. 17. Thus, the cannula 5 is firmly secured in place in the patient's arm 220 for intravenous feeding or the like.

When desired, the cannula 5 is then removed from the arm 220, much as it was inserted as in FIG. 16. The practitioner thus grasps the wings 50 and 60 as folded back in FIG. 18, and removes the needle. Then with the other hand the practitioner holds the catheter 230 steady while folding the wings 50 and 60 forward upon one another, similar to the original packing configuration of FIGS. 1A and 1B. At this point, the grooves 160 and 170 are configured to aligned with the distal end 20 such that the wings 50 and 60 may lie flush against one another, resulting in the configuration shown in FIGS. 4A and 4B. As seen most clearly in FIG. 5, at this point the locking tabs 200 and 210 interlock with the closure ports 190 and 180, respectively, thus forming a dependably enclosed needle. Grips 270 and 280 are provided on the wings 50 and 60, respectively, preferably taking the form of angular ridges.

In addition to the grips 270 and 280, additional central grips 320 and 330 may be provided on the wings 50 and 60, respectively, again comprising raised portions to allow the practitioner a more sure grip.

It will be appreciated that further grips (not separately shown) may be provided on the inside surfaces of the wings 50 and 60, i.e. on the surfaces opposite those on which grips 270 and 280 are positioned, so that when the cover is in the configuration of FIG. 9, the user of the needle will be provided with a sure means of grasping. This is of considerable assistance in emplacing and removing the needle, such as in FIG. 16. In order not to defeat the purpose of the closed configuration of FIGS. 4A and 4B, such an inside grip may be provided on the wings 50 and 60 such that the grip portion on one wing is received by a recess on the other wing, so as to allow the wings to close fully and interlock as desired.

As shown in FIGS. 11 and 13, in an alternative embodiment, each wing 50 and 60 may be provided with one locking tab (such as locking tabs 290 and 300, respectively), in which case each wing 50 and 60 is also provided with a closure port, such as the closure port 310 shown in FIG. 13. In either configuration, the snap closure of the wings by the practitioner protects him and others from accidentally being punctured by the distal end 20 of the cannula 5, and provides a safe configuration for disposing of the needle.

Figure 6:
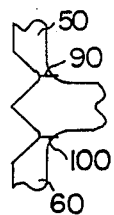
FIG. 6 is a view of the hinge utilized in the invention, and comprises a view taken essentially along the arc 6—6 of FIG. 11, with certain portions removed for clarity.

FIG. 6 shows a somewhat more detailed view of the hinge portion of the device, being a partial view of the area enclosed a circle 6—6 of FIG. 11. Hinges 90 and 100 are shown, and a possible configuration for portions of the wings 50 and 60 is shown.

When the sheath 30 is in place as in FIG. 1, preferably the wings 50 and 60 are prevented from interlocking with one another due to the fact that the sheath 30 has a diameter which is larger than the diameter of the grooves 160 and 170. An inner diameter of the sheath 30 is very closely matched to the outer diameter of the distal end 20, in order to discourage the practitioner from attempting to replace the sheath 30, which is likely to lead to injury.

Depending upon the packaging needs of the manufacturer, the needle with the cover 10 may also be shipped in the configuration shown in FIGS. 2A and 2B.

As seen in the view of FIG. 3B of the needle cover 10 just prior to insertion, the wings 50 and 60 when folded back form a grip with a relatively low angle of approach to the skin, which is quite convenient for insertion of the needle. In the preferred embodiments the angle A between the hinge 90 and the axis of the distal end 20 is about 30°.

The wide variety of configurations and uses for the needle of the present invention stem from the unique configuration thereof and the material from which it is formed. As discussed above, there are three important configurations which the needle 10 takes on, including the fully open position of FIG. 9, the fully closed position of FIGS. 4A, 4B and 5, and the in-use position of FIG. 17. As stated above, the wings 50 and 60, support portion 80, and shank 70 are preferably formed in an integral fashion from a resilient plastic. Since they are formed integrally, they may be produced in a single manufacturing step, for reducing costs and difficulty in manufacture.

The configuration of the device is such that the wings in their original and final, disposable configurations (see FIGS. 1 and 4, respectively), as mentioned above, enclose the distal end 20. The hinges 90 and 100, and the angles of the wings 50 and 60, are configured so that the wings 50 and 60 lie together when folded back, effectively forming a single handle for the medical practitioner. Finally, as shown in FIG. 17, a third configuration is taken on when one wing is folded down and the other is folded back, such that the wings may lie coplanar with one another and with the distal end 20 or the capability of using the integrally formed cover. Because of this, the wings 50 and 60 may be separately adhered to the skin 240 of the patient, preventing sliding and resultant injury of the needle. The combination of the structural characteristics of hinge and wing positions and angles is important for achieving these advantages of the invention. For instance, changing the angle of the wings 50 and 60 without also adjusting the angles of the hinges 90 and 100 would defeat one or more of the desired configurations, such as the protective enclosure over the distal end 20 of the needle. While a given angle may not be crucial, the combination of angles and structure shown is carefully designed to accomplish the advantages discussed.

It will be appreciated from the above that the present invention shows a new design which allows the medical practitioner to avoid accidental puncture at all times: when opening the needle and exposing the distal end 20, as in FIGS. 1-3; when actually inserting the needle into the arm of the patient as in FIG. 16, and when removing the needle from the patient, and when permanently closing the wings 50 and 60 over the distal end 20 for disposal in a safe and legal manner, as shown in FIGS. 18-20. Modifications may be made to the design of the present invention without departing the spirit and scope thereof.

I claim:

1. A cover for enclosing a disposable hypodermic needle having a cannula with a proximal end and a sharp distal end, including:
    a longitudinal shank having an axial cavity for mounting over a portion of the needle;
    a wing support portion formed integrally with said shank;
    at least two generally flat wings formed integrally with said support portion;
    at least two hinges, with one said hinge connecting each said wing with said support portion;
    where said shank, support portion, wings and hinges are formed from a resilient material, with each said hinge and wing is adapted to provide a first configuration wherein each said wing lies in a first position substantially in a plane containing the needle at a location immediately adjacent the distal end, and to provide a second configuration wherein a first said wing lies in said first position and a second said wing lies in a second position in said plane, where said second position is angled away from said distal end, and to provide a third configuration wherein each said wing lies in said second position with said wings adjacent one another for forming a grip for said cover for grasping by a user of said cover for insertion into or removal from a patient, where said second configuration is adapted for securing said cover against a needle entry site of the patient, and where said first configuration is adapted for enclosing the sharp distal end for preventing injury to the user.

2. The cover of claim 1, wherein each said wing includes means for receiving said distal end, such that when said cover is in said first configuration, said receiving means together enclose said distal end for preventing contact therewith by the user.

3. The cover of claim 2, wherein each said receiving means comprises a groove extending along a length of said wing, said groove having an inner diameter substantially conforming to an outer diameter of said distal end.

4. The cover of claim 1, wherein said first wing includes a means for interlocking with said second wing for maintaining said cover in said first configuration.

5. The cover of claim 4, wherein:
    said first wing includes at least one tab protruding at an angle therefrom; and
    said second wing includes at least one port for receiving said tab when said cover is in said first configuration, wherein said tab and said port are adapted for interlocking for preventing said cover from being opened from said first configuration.

6. The cover of claim 1, wherein at least one of said wings includes a means for grasping for allowing a sure grip by the user.

7. The cover of claim 6, wherein said grasping means is positioned such that when said cover is in said first configuration, said grasping means is outwardly disposed for gripping by the user.

8. The cover of claim 6, wherein said grasping means is positioned such that when said cover is in said third configuration, said grasping means is outwardly disposed for gripping by the user.

9. The cover of claim 8, said first wing includes said grasping means, and said second wing includes a recess for receiving said grasping means for allowing closure of said cover into said first configuration.

10. The cover of claim 6, wherein said grasping means is formed integrally with said wing.

11. The cover of claim 1, further including a removable sheath for enclosing said distal end for preventing injury to the user of the needle while handling before use in a patient.

12. The cover of claim 1, wherein said hinges are disposed at an oblique or nonaxial angle with respect to an axis of said distal end.

13. The cover of claim 12, wherein said angle is approximately 30°.

14. The cover of claim 1, wherein said shank includes a locking hub adjacent the proximal end of the needle, for coupling with a catheter for introducing a substance into a patient.

* * * * *